United States Patent
Chung (10) Patent No.: US 10,596,208 B2
(45) Date of Patent: *Mar. 24, 2020

(54) COMPOSITION FOR PREVENTING OR TREATING OBESITY OR LIPID-RELATED METABOLIC DISEASE

(71) Applicant: CELL BIOTECH CO., LTD., Gyeonggi-do (KR)

(72) Inventor: Myung Jun Chung, Seoul (KR)

(73) Assignee: Cell Biotech Co., Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/801,875

(22) Filed: Nov. 2, 2017

(65) Prior Publication Data

US 2018/0117102 A1    May 3, 2018

(30) Foreign Application Priority Data

Nov. 3, 2016 (KR) .......................... 10-2016-0146008

(51) Int. Cl.
| | |
|---|---|
| *A61K 35/747* | (2015.01) |
| *A61P 3/02* | (2006.01) |
| *A61K 31/519* | (2006.01) |
| *A61K 31/4415* | (2006.01) |
| *A61P 3/00* | (2006.01) |
| *A61K 31/197* | (2006.01) |
| *A61K 31/455* | (2006.01) |
| *A61K 35/74* | (2015.01) |
| *A61K 31/14* | (2006.01) |
| *A61K 31/714* | (2006.01) |
| *A61P 3/08* | (2006.01) |
| *A61P 9/10* | (2006.01) |
| *A61P 1/16* | (2006.01) |
| *A61P 9/00* | (2006.01) |
| *A61P 3/04* | (2006.01) |
| *A61P 3/06* | (2006.01) |
| *A61P 3/10* | (2006.01) |
| *A61P 9/12* | (2006.01) |
| *A61K 31/4188* | (2006.01) |
| *A61K 31/51* | (2006.01) |
| *A61K 31/525* | (2006.01) |
| *A61K 31/675* | (2006.01) |
| *A61K 35/744* | (2015.01) |

(52) U.S. Cl.
CPC ............ *A61K 35/747* (2013.01); *A61K 31/14* (2013.01); *A61K 31/197* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/675* (2013.01); *A61K 31/714* (2013.01); *A61K 35/74* (2013.01); *A61K 35/744* (2013.01); *A61P 1/16* (2018.01); *A61P 3/00* (2018.01); *A61P 3/02* (2018.01); *A61P 3/04* (2018.01); *A61P 3/06* (2018.01); *A61P 3/08* (2018.01); *A61P 3/10* (2018.01); *A61P 9/00* (2018.01); *A61P 9/10* (2018.01); *A61P 9/12* (2018.01)

(58) Field of Classification Search
None
See application file for complete search history.

(56) References Cited

U.S. PATENT DOCUMENTS

| | | | |
|---|---|---|---|
| 8,658,156 B2 * | 2/2014 | Salminen | ............... A61K 35/74 424/93.45 |
| 2011/0123501 A1 * | 5/2011 | Chou | ................... A61K 31/702 424/93.44 |
| 2013/0029906 A1 | 1/2013 | Simard et al. | |
| 2013/0089633 A1 * | 4/2013 | Nakamura | ........... A23D 7/0056 424/780 |
| 2014/0079676 A1 | 3/2014 | Olmstead | |

FOREIGN PATENT DOCUMENTS

| | | |
|---|---|---|
| EP | 2022502 | 2/2009 |
| KR | 10-2008-0016391 | 2/2008 |
| KR | 10-2010-0109661 | 10/2010 |
| KR | 10-2013-0046896 | 5/2013 |
| KR | 10-1611837 | 4/2016 |
| WO | WO 2010/124387 | 11/2010 |
| WO | WO 2015/172191 | 11/2015 |
| WO | WO 2016/020488 | 2/2016 |
| WO | WO 2016/020489 | 2/2016 |

OTHER PUBLICATIONS

WebMD "Fatty Liver Disease (Hepatic Steatosis)" 4 pgs, 2018 (Year: 2018).*
Gyegang "Vitamin B group such as B2 and pantothenic acid; Lower cholesterol." NAVER Blog, May 2009, 2 pages (English translation).
Hlivak et al. "One-year application of probiotic strain Enterococcus faecium M-74 decreases serum cholesterol levels," Bratisl Lek Listy, 2005, vol. 106, No. 2, pp. 67-72.
Kekkonen et al. "Effect of probiotic Lactobacillus rhamnosus GG intervention on global serum lipidomic profiles in healthy adults," World Journal of Gastroenterology, May 2008, vol. 14, No. 20, pp. 3188-3194.
Official Action for Korea Patent Application No. 10-2016-0146008, dated Jan 8, 2018, 6 pages.
Chang et al. "Effect of functional yogurt NY-YP901 in improving the trait of metabolic syndrome," European Journal of Clinical Nutrition, Jun. 2011, vol. 65, No. 11, pp. 1250-1255.

(Continued)

*Primary Examiner* — Thane Underdahl
(74) *Attorney, Agent, or Firm* — Sheridan Ross P.C.

(57) ABSTRACT

The present invention provides a pharmaceutical composition and a food composition for preventing or treating lipid-related metabolic disease, which contain, as active ingredients, probiotics and a vitamin B complex. When the composition comprising the probiotics and the vitamin B complex is used, it may further promote in vivo absorption of the vitamin B complex, and may induce a synergistic effect on a reduction in blood lipid levels, thereby exhibiting an effect on the alleviation, prevention or treatment of obesity and lipid-related metabolic disease.

3 Claims, 6 Drawing Sheets

(56) References Cited

OTHER PUBLICATIONS

Iacono et al. "Probiotics as an emerging therapeutic strategy to treat NAFLD: focus on molecular and biochemical mechanisms," Journal of Nutritional Biochemistry, Aug. 2011, vol. 22, No. 8, pp. 699-711.
Safavi et al. "The effects of synbiotic supplementation on some cardio-metabolic risk factors in overweight and obese children: a randomized triple-masked controlled trial," International Journal of Food Sciences and Nutrition, Mar. 2013, vol. 64, No. 6, pp. 687-693.
Partial Search Report for European Patent Application No. 17198838.9, dated Mar. 23, 2018, 16 pages.
International Search Report for International (PCT) Patent Application No. PCT/KR2017/012157, dated Jan. 4, 2018, 4 pages.
Agerholm-Larsen et al. "Effect of 8 week intake of probiotic milk products on risk factors for cardiovascular diseases," European journal of Clinical Nutrition, Apr. 2000, vol. 54, No. 4, pp. 288-297.
Cheik et al. "Effects of a ferment soy product on the adipocyte area reduction and dyslipidemia control in hypercholesterolemic adult male rats," Lipids in Health and Disease, Dec. 2008, vol. 7, No. 1, 9 pages.
Extended Search Report for European Patent Application No. 17198838.9, dated Jul. 16, 2018, 25 pages.

* cited by examiner

COMPOSITION FOR PREVENTING OR TREATING OBESITY OR LIPID-RELATED METABOLIC DISEASE

CROSS-REFERENCE TO RELATED APPLICATIONS

This application claims the benefit of the Republic of Korea Patent Application No. 10-2016-0146008 filed on Nov. 3, 2016, the entire contents of which are incorporated herein by reference.

TECHNICAL FIELD

The present invention relates to a composition for preventing or treating obesity or lipid-related metabolic disease.

BACKGROUND OF THE INVENTION

In recent years, the prevalence of obesity has greatly increased due to the Westernization of eating habits and the lack of activity. Obesity causes hypertension, diabetes, cardiovascular diseases and various cancers, and for this reason, interest in the prevention and treatment of obesity has increased in the world.

Although obesity itself increases the body weight, makes the body obese, and thus makes life inconvenient, the bigger problem is that obesity increases blood lipid levels to cause arteriosclerosis and heart disease, increases insulin resistance to cause complications such as diabetes, menstrual irregularity and cancer, and causes chronic adult diseases such as hyperlipidemia, hypertension, coronary artery disease and stroke. For this reason, the treatment and prevention of obesity are essential (Lee J H, J. Kor. Soc. Obes., 1:21-24, 1992; Lew E A, Ann. Intern. Med., 103:1024-1029, 1985; Kim K I et al., Korean J. Food Sci. Technol., 35:720-725, 2003).

Obesity is known to be caused by genetic factors, environmental factors resulting from Westernized eating habits, psychological factors resulting from stress, and the like, but the exact causes or mechanisms of obesity have not been clearly found.

In the past, it has been recognized that adipocytes merely act to store surplus energy of the human body in the form of triglycerides and to buffer external impact. However, in the recent years, adipocytes have been recognized as an endocrine organ that secretes adipocytokines which regulate fasting metabolism and insulin sensitivity. Specifically, adipocytokines such as adiponectin, leptin, resistin, tumor necrosis factor alpha (TNF-$\alpha$), interleukin-6 (IL-6) and the like are known to play an important role in maintaining homeostasis and regulating energy metabolism (Matsuzawa, Y. et al., Ann. Ny. Acad. Sci., 892:146-154, 1999; Saltiel, A. R., Nat. Med., 7:887-888, 2001).

The goals for treating obesity can be largely classified into two. The first goal is to burn an excess amount of fat to reduce body weight, and the second goal is to improve metabolic imbalance. Currently, the treatment of obesity aims not only at reducing body weight, but also at improving metabolic abnormalities by early eliminating factors that cause cardiovascular diseases. In addition, studies have been actively conducted to inhibit obesity by controlling food intake and energy expenditure.

Hypothalamus, motor nervous, autonomic nervous and peripheral nervous systems are all involved in regulation of food intake behaviors. Particularly, the hypothalamus of the central nervous system plays an important role in the pathology of obesity. Typical factors that are secreted from the hypothalamus include neuropeptide Y, POMC/CART, melanocortin receptor, norepinephrine, serotonin, and the like. Current strategies for development of obesity therapeutic agents include reduced food intake, a reduction in caloric absorption, promotion of exothermic reactions, regulation of energy metabolism, regulation of signaling through the nervous system, and the like (Mi-Jung Park, Korean J Pediatr 48(2), 2005).

Obesity therapeutic drugs known to date are largely divided according to the mechanism of action into satiety stimulants, fat absorption inhibitors, and antipsychotic appetite suppressants. The most representative drugs for obesity treatment include Xenical™ (Roche Pharmaceuticals, Switzerland), Reductil™ (Abbott, USA), Exolise™ (Arkopharma, France) and the like, but have problems in that they cause fatty stool, intestinal gas generation, abdominal bloating, fecal incontinence and the like, and causes adverse effects such as cardiac diseases, respiratory diseases, neurological diseases and the like, and the persistence of efficacy thereof is low.

Accordingly, in order to minimize the adverse effects of artificially synthesized substances as described above, functional substances effective for weight control have been developed from natural substances. However, anti-obesity substances extracted from such natural substances have problems in that the effective concentration of components that exhibit efficacy is low and many costs are incurred because the natural substances are cultivated in farmlands or the like.

SUMMARY OF THE INVENTION

One embodiment of the invention relates to a method for preventing or treating obesity or lipid-related metabolic disease, the method comprising a step of administering to a subject in need of treatment a composition containing probiotics and a vitamin B complex.

In one aspect, the probiotics comprise one or more lactic acid bacteria strains selected from the group consisting of *Streptococcus* spp., *Lactococcus* spp., *Enterococcus* spp., *Lactobacillus* spp., *Pediococcus* spp., *Leuconostoc* spp., *Weissella* spp., and *Bifidobacterium* spp.

In one aspect, the probiotics comprise *Enterococcus faecium*, *Lactobacillus rhamnosus*, or a mixture thereof.

In one aspect, the probiotics are contained in an amount of $3 \times 10^9$ to $6 \times 10^9$ CFU/g based on the total weight of the composition.

In one aspect, the vitamin B complex comprises two or more selected from the group consisting of vitamin B1, vitamin B2, vitamin B3, vitamin B6, vitamin B7, vitamin B12, salts thereof, and derivatives thereof.

In one aspect, the lipid-related metabolic disease is any one selected from the group consisting of diabetes, hyperlipidemia, fatty liver, hepatitis, liver cirrhosis, arteriosclerosis, hypertension, cardiovascular diseases, and metabolic syndromes in which the diseases occur simultaneously.

DETAILED DESCRIPTION OF THE INVENTION

It is an object of the present invention to provide a pharmaceutical composition capable of preventing or treating obesity or lipid-related metabolic disease, which has an excellent effect of reducing blood lipid and cholesterol levels.

Another object of the present invention is to provide a food composition capable of alleviating or preventing obesity or lipid-related metabolic disease, which has an excellent effect of reducing blood lipid and cholesterol levels.

However, objects which are to be achieved by the present invention are not limited to the above-mentioned objects, and other objects of the present invention will be clearly understood by those skilled in the art from the following description.

The present inventors have conducted studies, and as a result, have found that when a combination of probiotics and a vitamin B complex is used, it has an excellent effect of promoting the absorption of the vitamin B complex and has a synergistic effect on a reduction in blood lipid levels, thereby completing the present invention.

In one embodiment, the present invention is directed to a pharmaceutical composition for preventing or treating obesity or lipid-related metabolic disease, which contains, as active ingredients, probiotics and a vitamin B complex.

As used herein, the term "probiotics" refers to living microbial food supplements that beneficially affect the host by improving its intestinal microbial balance. In a broader sense, the term may be defined as living microorganisms which, when ingested in certain numbers, exert health benefits beyond inherent basic nutrition. Cocktails of various microorganisms, particularly species of *Lactobacillus* and *Bifidobacterium*, have traditionally been used in fermented dairy products to promote human health. However, to be effective, the probiotics must survive under manufacturing processes, packaging and storage conditions and must also viably pass through gastrointestinal tracts so as to viably remain so that probiotic substances have positive health effects.

In the present invention, the probiotics lactic acid bacteria strains may be cultured by a general culture method for lactic acid bacteria, and recovered by a separation process such as centrifugation. The recovered lactic acid bacteria may be dried by, but not limited to, freeze-drying, and may be used as probiotics.

The kinds of probiotics that are used in the present invention are not particularly limited. For example, the probiotics may comprise one or more lactic acid bacteria strains selected from the group consisting of *Streptococcus* spp., *Lactococcus* spp., *Enterococcus* spp., *Lactobacillus* spp., *Pediococcus* spp., *Leuconostoc* spp., *Weissella* spp., and *Bifidobacterium* spp. Preferably, the probiotics may comprise *Enterococcus faecium*, *Lactobacillus rhamnosus*, or a mixture thereof.

In the present invention, the probiotics may be contained in an amount of $3 \times 10^9$ to $6 \times 10^9$ CFU/g based on the total weight of the composition, but are not limited thereto. If the content of the probiotics is less than $3 \times 10^9$ CFU/g, the effect of increasing antioxidant effects cannot be obtained, because the content thereof is low, and if the content of the probiotics is more than $6 \times 10^9$ CFU/g, the appearance of the composition can be poor.

Furthermore, the vitamin B complex that is used in the present invention may comprise two or more selected from the group consisting of thiamine (vitamin B1), riboflavin (vitamin B2), niacin (vitamin B3), pyridoxine (vitamin B6), biotin (vitamin B7), cyanocobalamin (vitamin B12), salts thereof, and derivatives thereof, but is not limited thereto.

In the present invention, vitamin B1 (thiamin) prevents and treats beriberi that is a neurological disease, and vitamin B2 (riboflavin), also called vitamin G, is a component of coenzyme that plays an important role in various metabolisms, and it is involved in a metabolism in which cells are supplied with energy from an energy source. Furthermore, vitamin B6 is composed of three components, pyridoxine, pyridoxal and pyridoxamine, and may be involved in amino acid metabolisms, heme synthesis, carbohydrate metabolisms, neurotransmitter synthesis, vitamin formation, immunometabolism and lipid metabolisms. Moreover, vitamin B7, also called biotin or vitamin H, acts as enzyme and cofactor and may be used for treatment of diabetes and brittle nails. In addition, vitamin B12 (cyanocobalamin) is known to be essential for normal growth of animals and to be involved in lipid or carbohydrate metabolisms, including production of blood cells, maturation of bowel epithelial cells, and synthesis of nucleic acids or proteins. Vitamin B12 may be synthesized in intestinal microorganisms, but lack of vitamin B12 may show symptoms, including megaloblastic anemia, red tongue, movement disorder, coma, acidosis, developmental disorder, vomiting and the like.

In the present invention, the use of probiotics in combination with the vitamin B complex may have a great synergistic effect on a reduction in blood lipid levels, and more specifically, may promote esterification of blood cholesterol with respect to the levels of blood LDL (low-density lipoprotein) cholesterol, LDL (low-density lipoprotein)/VLDL (very-low-density lipoprotein) cholesterols and triglycerides to thereby inhibit acyl-CoA-cholesterol acyltransferase (ACAT) that is involved in cholesterol absorption, thereby reducing blood lipid levels (Witiak D. T. and D. R. Feller (eds), Anti lipidemic Drugs: Medicinal, Chemical, and Biochemical Aspects, Elsevier, 159-1 95, 1991).

As used herein, the term "obesity" may refer to a condition or disease with excessive body fat resulting from energy imbalance.

As used herein, the term "lipid-related metabolic disease" refers to a disease caused by excessive lipid accumulation in a living body. Specifically, the lipid-related metabolic disease may be any one selected from the group consisting of diabetes, hyperlipidemia, fatty liver, hepatitis, liver cirrhosis, arteriosclerosis, hypertension, cardiovascular diseases, and metabolic syndromes in which the above-described diseases occur simultaneously, but is not limited thereto.

As used herein, the term "preventing" may refer to all actions that block symptoms of obesity or lipid-related metabolic disease or inhibit or delay the symptoms by use of the pharmaceutical composition according to the present invention.

As used herein, the term "treating" may refer to all actions that alleviate or beneficially change symptoms of obesity or lipid-related metabolic disease by use of the pharmaceutical composition according to the present invention.

For use, the pharmaceutical composition of the present invention may be formulated into oral preparations such as powders, granules, capsules, tablets, aqueous suspensions and the like, and forms such as external preparations, suppositories and sterile injectable solutions, according to conventional methods, but is not limited thereto. The pharmaceutical composition of the present invention may contain a pharmaceutically acceptable carrier. For oral administration, the pharmaceutically acceptable carrier may include a binder, a lubricant, a disintegrant, an excipient, a solubilizer, a dispersing agent, a stabilizer, a suspending agent, a coloring agent, a flavoring agent and the like. For injectable preparations, the pharmaceutically acceptable carrier may include a buffering agent, a preservative, an analgesic, a solubilizer, an isotonic agent, a stabilizer and the like. For topical administration, the pharmaceutically acceptable carrier may include a base, an excipient, a lubricant, a preservative and the like. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups, wafers or the like. For injectable administration, the pharmaceutical composition may be formulated as a unit dosage ampoule or a multiple dosage form. In addition, the pharmaceutical composition may also be formulated into solutions, suspensions, tablets, capsules and sustained-release preparations.

Meanwhile, examples of the carrier, excipient, and diluent suitable for the formulation may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil or the like. In addition, the pharmaceutical composition of the present invention may further contain a filler, an anti-agglutinating agent, a lubricating agent, a wetting agent, a flavoring agent, an emulsifying agent, a preservative or the like.

Routes of administration of the pharmaceutical composition according to the present invention include, but are not limited to, oral, intravenous, intramuscular, intra-arterial, intramarrow, intrathecal, intracardiac, transdermal, subcutaneous, intraperitoneal, intranasal, intraintestinal, topical, sublingual or rectal routes. Oral or parenteral administration is preferred.

As used herein, the term "parenteral" includes subcutaneous, intracutaneous, intravenous, intramuscular, intraarticular, intrasynovial, intrasternal, intrathecal, intralesional, and intracranial injection or infusion techniques. The pharmaceutical composition of the present invention may also be administered in the form of suppositories for rectal administration.

The pharmaceutical composition of the present invention may vary depending on various factors, including the activity of a particular compound used, the patient's age, weight, general health, sex, diet, administration time, administration mode, excretion rate, drug combination and the severity of a particular disease to be prevented or treated. The dose of the pharmaceutical composition may be suitably selected by a person skilled in the art depending on the patient's condition, weight, the severity of the disease, the type of drug, administration mode and period, and the pharmaceutical composition may be administered at a dose of 0.0001 to 50 mg/kg or 0.001 to 50 mg/kg per day. The pharmaceutical composition may be administered once or several times per day. The dose does not limit the scope of the present invention in any way. The pharmaceutical composition according to the present invention may be formulated as pills, coated tablets, capsules, liquids, gels, syrups, slurries or suspensions.

In another embodiment, the present invention is directed to a food composition for preventing or alleviating obesity or lipid-related metabolic disease, which contains, as active ingredients, probiotics and a vitamin B complex.

In the food composition of the present invention, the contents regarding the above-described probiotics, vitamin B complex, obesity and lipid-related metabolic disease are as described above with respect to the pharmaceutical composition, and thus the specific description thereof will be omitted below.

As used herein, the term "alleviating" may refer to all actions that alleviate or beneficially change symptoms of obesity or lipid-related metabolic disease by use of the food composition according to the present invention.

The food composition according to the present invention may be prepared as various foods, for example, beverages, gums, teas, vitamin complexes, powders, granules, tablets, capsules, confectionery, cakes, bread and the like. When the compound of the present invention is contained in a food composition, it may be added in an amount of 0.1 to 50 wt % based on the total weight.

When the food composition is prepared as a beverage, there is no particular limitation, except that the beverage contains the food composition at the indicated percentage. The beverage may additionally contain various flavorings or natural carbohydrates, like conventional beverages. Examples of the natural carbohydrates include monosaccharides such as glucose, disaccharides such as fructose, polysaccharides such as sucrose, conventional sugars such as dextrin, cyclodextrin or the like, and sugar alcohols such as xylitol, sorbitol, erythritol or the like. Examples of the flavorings include natural flavorings (thaumatin, stevia extracts, such as rebaudioside A, glycyrrhizin, etc.) and synthetic flavorings (saccharin, aspartame, etc.).

In addition, the food composition of the present invention may contain various nutrients, vitamins, minerals (electrolytes), flavorings such as synthetic flavorings and natural flavorings, colorants, pectic acid and its salt, alginic acid and its salt, organic acids, protective colloidal thickeners, pH adjusting agents, stabilizers, preservatives, glycerin, alcohol, carbonizing agents that are used in carbonated beverages, etc.

Such components may be used individually or in combination. Although the percentage of such additives is not of great importance in the present invention, it is generally selected in a range of 0.1 to about 50 parts by weight based on 100 parts by weight of the food composition of the present invention.

In addition, the food composition of the present invention can be administered orally as a food or nutritional product, such as milk or whey-based fermented dairy product, or as a food supplement or a health functional food. Specifically, foods such as milk-based products, beverages, juices, soups, or foods for children may be exemplified, but are not limited thereto. The "milk-based product" means any liquid or semi-solid milk or whey-based product having a varying fat content. The milk-based product can be, for example, cow's milk, goat's milk, sheep's milk, cream, full-fat milk, whole milk, low-fat milk or skim milk, ultrafiltered milk, diafiltered milk, microfiltered milk, milk recombined from powdered milk or whey through any processing, or a processed product, such as yoghurt, curdled milk, sour milk, sour whole milk, butter milk, other fermented milk products, such as viili, filling of snack bars, etc. Another important group includes milk beverages, such as whey beverages, fermented milks, condensed milks, infant or baby milks; icecream; milk-containing food such as sweets.

In still another embodiment, the present invention is directed to a method for preventing or treating obesity or lipid-related metabolic disease, comprising a step of administering to a subject in need of treatment a composition containing probiotics and as vitamin B complex.

As used herein, the expression "subject in need of treatment" means a subject having obesity and lipid-related metabolic disease or suspected of having symptoms thereof, in which the lipid-related metabolic disease means a disease caused by excessive lipid accumulation in a living body. Specifically, the lipid-related metabolic disease may be any one selected from the group consisting of diabetes, hyperlipidemia, fatty liver, hepatitis, liver cirrhosis, arteriosclerosis, hypertension, cardiovascular diseases, and metabolic syndromes in which the above-described diseases occur simultaneously, but is not limited thereto.

In the present invention, co-administration of the probiotics with the vitamin B complex may have a great synergistic effect on a reduction in blood lipid levels of the subject, and thus can effectively prevent or treat obesity and lipid-related metabolic disease.

In the present invention, the contents regarding the above-described probiotics and vitamin B complex are as described above with respect to the pharmaceutical composition, and thus the specific description thereof will be omitted below.

In the present invention, routes of administration of the composition include, but are not limited to, oral, intravenous, intramuscular, intra-arterial, intramarrow, intrathecal, intracardiac, transdermal, subcutaneous, intraperitoneal, intranasal, intraintestinal, topical, sublingual or rectal routes. Oral or parenteral administration is preferred.

As used herein, the term "parenteral" includes subcutaneous, intracutaneous, intravenous, intramuscular, intraarticular, intrasynovial, intrasternal, intrathecal, intralesional, and intracranial injection or infusion techniques. The pharmaceutical composition of the present invention may also be administered in the form of suppositories for rectal administration.

The pharmaceutical composition of the present invention may vary depending on various factors, including the activity of a particular compound used, the patient's age, weight, general health, sex, diet, administration time, administration mode, excretion rate, drug combination and the severity of a particular disease to be prevented or treated. The dose of the pharmaceutical composition may be suitably selected by a person skilled in the art depending on the patient's condition, weight, the severity of the disease, the type of drug, administration mode and period, and the pharmaceutical composition may be administered at a dose of 0.0001 to 50 mg/kg or 0.001 to 50 mg/kg per day. The pharmaceutical composition may be administered once or several times per day. The dose does not limit the scope of the present invention in any way.

In the present invention, the composition may be in the form of capsules, tablets, granules, injectable solutions, ointments, powders or beverages, and the pharmaceutical composition may be for use in humans.

For use, the composition of the present invention may be formulated into oral preparations such as powders, granules, capsules, tablets, aqueous suspensions and the like, and forms such as external preparations, suppositories and sterile injectable solutions, according to conventional methods, but is not limited thereto. The pharmaceutical composition of the present invention may contain a pharmaceutically acceptable carrier. For oral administration, the pharmaceutically acceptable carrier may include a binder, a lubricant, a disintegrant, an excipient, a solubilizer, a dispersing agent, a stabilizer, a suspending agent, a coloring agent, a flavoring agent and the like. For injectable preparations, the pharmaceutically acceptable carrier may include a buffering agent, a preservative, an analgesic, a solubilizer, an isotonic agent, a stabilizer and the like. For topical administration, the pharmaceutically acceptable carrier may include a base, an excipient, a lubricant, a preservative and the like. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups, wafers or the like. For injectable administration, the pharmaceutical composition may be formulated as a unit dosage ampoule or a multiple dosage form. In addition, the pharmaceutical composition may also be formulated into solutions, suspensions, tablets, capsules and sustained-release preparations.

Meanwhile, examples of the carrier, excipient, and diluent suitable for the formulation may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil or the like. In addition, the composition of the present invention may further contain a filler, an anti-agglutinating agent, a lubricating agent, a wetting agent, a flavoring agent, an emulsifying agent, a preservative or the like.

When the composition comprising the probiotics and the vitamin B complex according to the present invention is used, it may further promote in vivo absorption of the vitamin B complex, and may induce a synergistic effect on a reduction in blood lipid levels, thereby exhibiting an effect on the alleviation, prevention or treatment of obesity and lipid-related metabolic disease.

Hereinafter, the present invention will be described in further detail with reference to examples. It will be obvious to those skilled in the art that these examples are for illustrative purposes only and are not intended to limit the scope of the present invention.

EXAMPLES

Preparation Example 1: Preparation of Test Animals

In order to verify the effect of a combination of probiotics and a vitamin B complex on the prevention and treatment of hyperlipidemia-related lipid metabolism disorder, 4-week-old white rats (male, SD rats, Saeronbio, Korea) were purchased. Two of the animals were housed in each polypropylene cage and acclimated for one week while they were allowed access to feed and water ad libitum. Next, in order to induce hyperlipidemia-related lipid metabolism disorder in the white rats, D12492 (Saeronbio, Korea) having a high fat content of 60% was fed as basal diet while the animals were allowed access to water ad libitum. In addition, the animals were housed at a temperature of 24±2° C. and a relative humidity of 40±20% with a 12-hr light/12-hr dark cycle. During the acclimation period, the health of the rats was checked, and among these rats, animals whose activity was not reduced were selected and used in subsequent tests.

Example 1: Oral Administration of Probiotics and Vitamin B Complex

In order to verify the effects of probiotics and a vitamin B complex on the alleviation, prevention and treatment of obesity and lipid-related metabolic disease in the white rats selected in Preparation Example 1 above, as shown in Table 1 below, each of PBS (G1) which is a negative control, and $5 \times 10^9$ CFU of *L. rhamnosus* and *E. facecium* (G2), a vitamin B complex (G3) comprising thiamine hydrochloride (B1), riboflavin (B2), pyridoxine hydrochloride (B6) and biotin (B7), and a mixture of G2 and G3, which are test substances, was administered orally to the white rats for 5 weeks.

TABLE 1

| Group | Substance administered | Dose |
|---|---|---|
| G1 (N = 5) | PBS | — |
| G2 (N = 5) | *L. rhamnosus* and *E. facecium* | $5 \times 10^9$ CFU/head |
| G3 (N = 5) | Thiamine hydrochloride (B1) | 18 mg/head |
| | Riboflavin (B2) | 21 mg/head |
| | Pyridoxine hydrochloride (B6) | 22.5 mg/head |
| | Biotin (B7) | 45 µg/head |
| G4 (N = 5) | G2 + G3 | $5 \times 10^9$ CFU/head + B complex |

Test Example 1: Biochemical Analysis of Serum of White Rats

In order to examine the effect of a mixture of probiotics and a vitamin B complex on the inhibition of lipid metabolism, the white rats in Example 1 were fasted for 14 hours, and then blood was collected from the abdominal aorta under carbon dioxide anesthesia. The collected blood was allowed to stand at room temperature for 30 minutes, and then centrifuged at 3,000 RPM for 30 minutes to separate sera, and the sera were stored at −80° C.

In order to confirm changes in lipid metabolism in the sera obtained as described above, the levels of CHOL (total cholesterol), HDL (high-density lipoprotein)-cholesterol, LDL (low-density lipoprotein)-cholesterol and triglyceride (TG) in the sera were measured using an automatic biochemical analyzer (Modular Analytic, Roche, Germany). Furthermore, atherogenic index (AI) in the sera was measured as described below according to the method of Haglund et al. The results of the measurement are shown in Tables 2 to 6 below and FIGS. 1 to 5.

Figure 1:
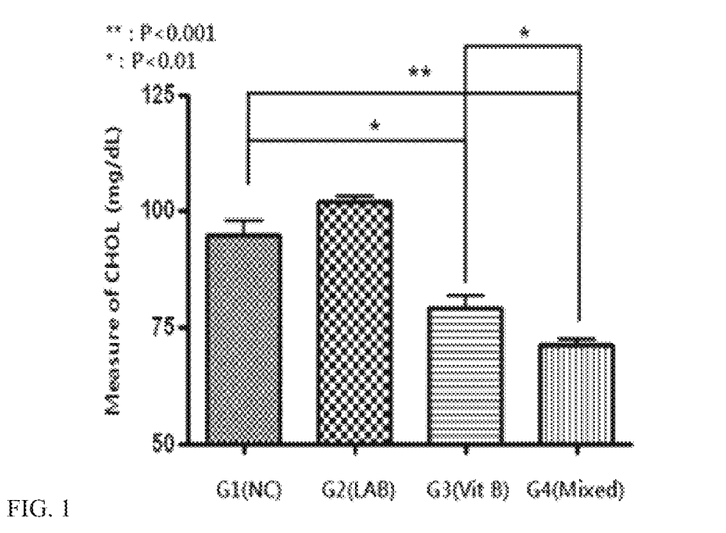
FIG. 1 graphically shows a change in the serum CHOL (total cholesterol) level of each white rat administered with probiotics and a vitamin B complex in Test Example 1.
Figure 2:
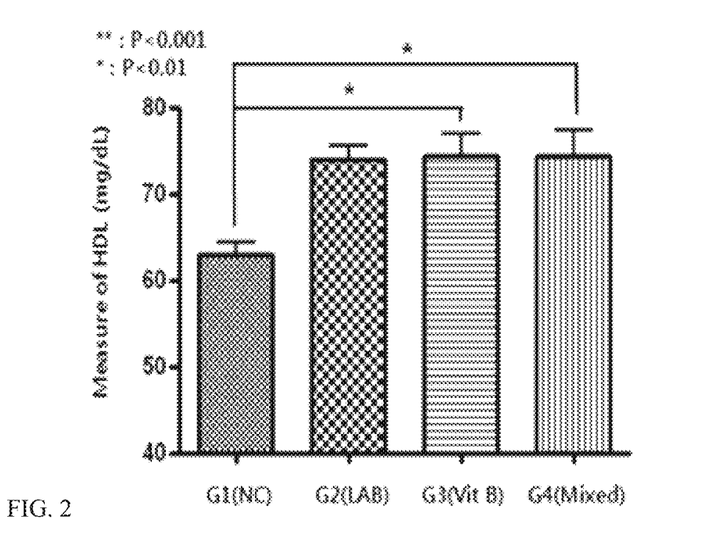
FIG. 2 graphically shows a change in the serum HDL (high-density lipoprotein) level of each white rat administered with probiotics and a vitamin B complex in Test Example 1.
Figure 3:
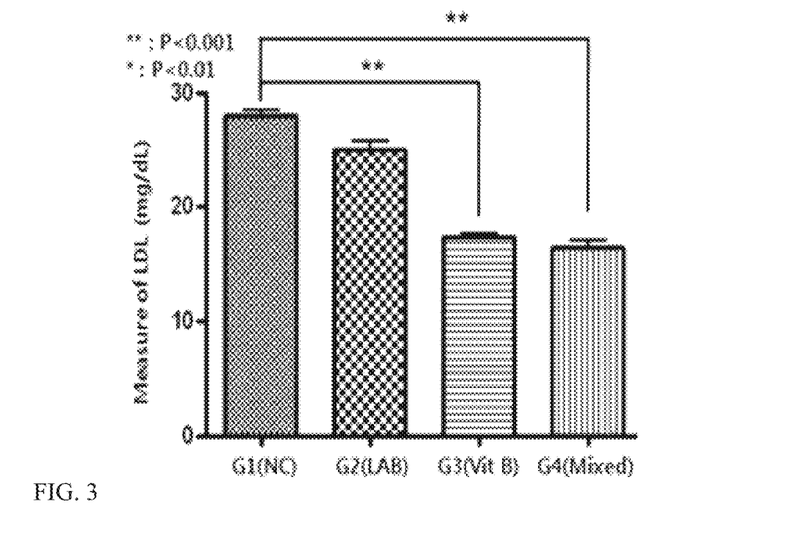
FIG. 3 graphically shows a change in the serum LDL (low-density lipoprotein) level of each white rat administered with probiotics and a vitamin B complex in Test Example 1.
Figure 4:
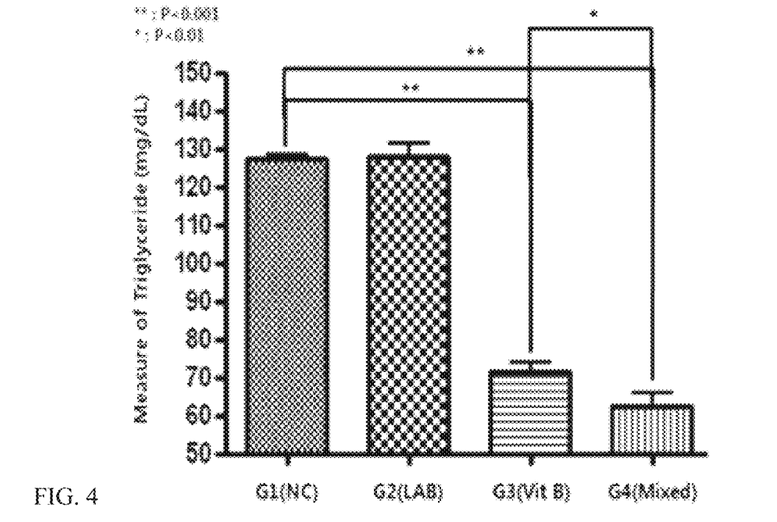
FIG. 4 graphically shows a change in the serum triglyceride level of each white rat administered with probiotics and a vitamin B complex in Test Example 1.
Figure 5:
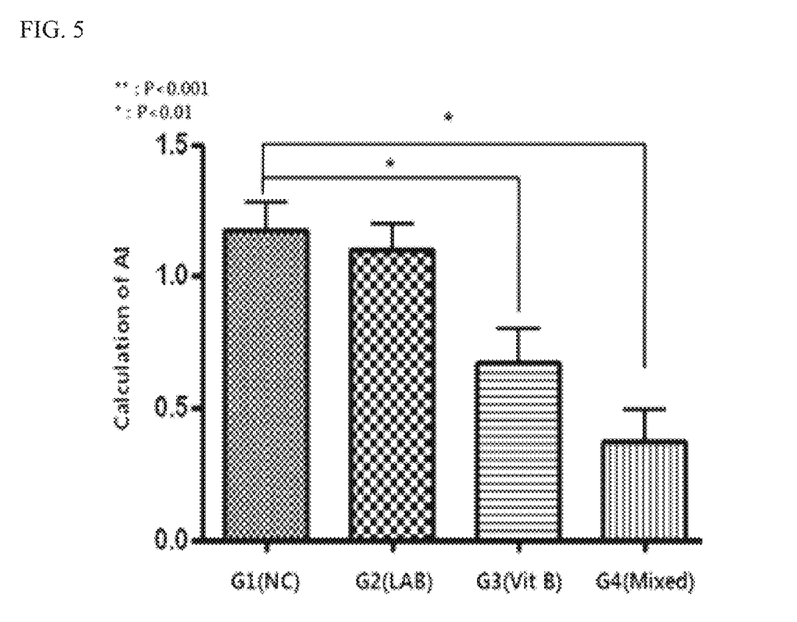
FIG. 5 graphically shows the results of measuring the serum atherogenic index (AI) of each white rat administered with probiotics and a vitamin B complex in Test Example 1.

AI (atherogenic index)={(total cholesterol level)−(HDL-cholesterol level)}/(HDL-cholesterol level)

TABLE 2

| | Mean ± SD | | | | |
|---|---|---|---|---|---|
| | G1 (NC) | G2 (LAB) | G3 (Vit B) | G4 (mixed) | P Value |
| CHOL (mg/dL) | 94.75 ± 6.13 | 102 ± 2.16 | 79 ± 5.16 | 71.33 ± 2.45 | <0.0001 |

TABLE 3

| | Mean ± SD | | | | |
|---|---|---|---|---|---|
| | G1 (NC) | G2 (LAB) | G3 (Vit B) | G4 (mixed) | P Value |
| HDL (mg/dL) | 69 ± 2.58 | 74 ± 2.65 | 74.25 ± 5.32 | 74.33 ± 5.13 | 0.0082 |

TABLE 4

| | Mean ± SD | | | | |
|---|---|---|---|---|---|
| | G1 (NC) | G2 (LAB) | G3 (Vit B) | G4 (mixed) | P Value |
| LDL (mg/dL) | 28 ± 0.82 | 25 ± 1.41 | 17.33 ± 0.58 | 16.5 ± 1 | <0.0001 |

TABLE 5

| | Mean ± SD | | | | |
|---|---|---|---|---|---|
| | G1 (NC) | G2 (LAB) | G3 (Vit B) | G4 (mixed) | P Value |
| TG (mg/dL) | 127.3 ± 2.5 | 127.8 ± 7.04 | 71.33 ± 4.04 | 62.5 ± 5.5 | <0.0001 |

TABLE 6

| | Mean ± SD | | | | |
|---|---|---|---|---|---|
| | G1 (NC) | G2 (LAB) | G3 (Vit B) | G4 (mixed) | P Value |
| AI | 1.1757 ± 0.25 | 1.1 ± 0.2 | 0.675 ± 0.25 | 0.375 ± 0.24 | 0.0008 |

As shown in FIGS. 1 to 4 and Tables 2 to 5 above, the blood cholesterol levels were significantly reduced when the mixture of the probiotics and the vitamin B complex (G4) was administered compared to when the probiotics (G2) and the vitamin B complex (G3) were administered alone. Furthermore, the results of measurement of the blood triglyceride level indicated that the blood triglyceride level in the group administered with the mixture of the probiotics and the vitamin B complex was lower by about 10 mg/dL than that in the groups administered with the probiotics and the vitamin B complex alone.

In addition, as shown in FIG. 5 and Table 6 above, the atherogenic index (AI) in the group administered with the mixture of the probiotics and the vitamin B complex was 0.375±0.24, which was lower by about 0.4 or more than that in the groups administered with the probiotics and the vitamin B complex alone.

The above-described results indicate that the use of the probiotics in combination with the vitamin B complex in the present invention has difficult-to-predict synergistic effects in reductions in blood cholesterol, LDL and TG levels and an increase in HDL level, compared when the probiotics and the vitamin B complex are used alone, suggesting that use of the probiotics in combination with the vitamin B complex has an excellent effect on the alleviation of obesity and lipid-related metabolic disorders.

Test Example 2: Absorption Rate of Vitamin B Complex in Serum of White Rats

In order to examine the absorption rate of the vitamin B complex in the blood collected in Example 1, the levels of vitamin B1 and B6 in the serum were measured by high-performance liquid chromatography (HPLC) using vitamin B1 and B6 measurement kits. In addition, the level of vitamin B2 in the serum was measured by radioimmunoassay (MA) using a 1,25-dihydroxy vitamin D 123-I MA kit. The results of the measurement are shown in Tables 7 to 9 below and FIGS. 6 to 8.

TABLE 7

| | G1 (NC) | G2 (LAB) | G3 (Vit B) | G4 (mixed) | P Value |
|---|---|---|---|---|---|
| Vitamin B1 (µg/L) | 137.7 ± 14.22 | 132.7 ± 7.96 | 173.4 ± 7.82 | 197.1 ± 7.03 | <0.0001 |

TABLE 8

| | G1 (NC) | G2 (LAB) | G3 (Vit B) | G4 (mixed) | P Value |
|---|---|---|---|---|---|
| Vitamin B2 (µg/L) | 100.7 ± 2.05 | 102 ± 1.02 | 106.8 ± 1.79 | 124.2 ± 0.618 | <0.0001 |

TABLE 9

| | G1 (NC) | G2 (LAB) | G3 (Vit B) | G4 (mixed) | P Value |
|---|---|---|---|---|---|
| Vitamin B6 (µg/L) | 788 ± 104.0 | 785.2 ± 100.7 | 1002 ± 83.51 | 1370 ± 177.9 | <0.0001 |

Figure 6:
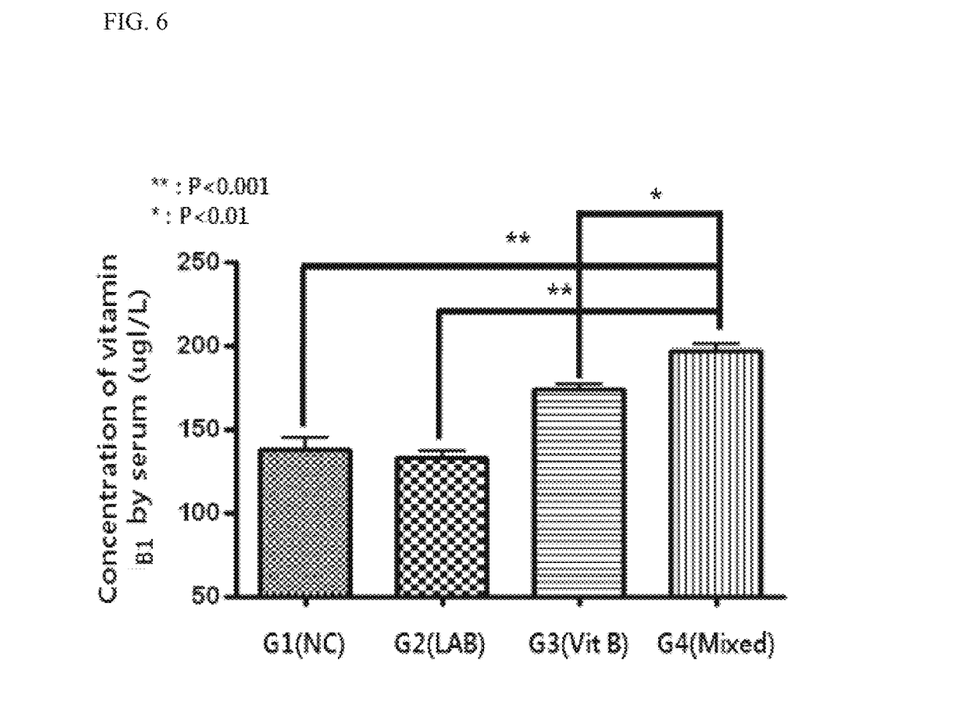
FIG. 6 graphically shows a change in the serum vitamin B1 level of each white rat administered with probiotics and a vitamin B complex in Test Example 2.
Figure 7:
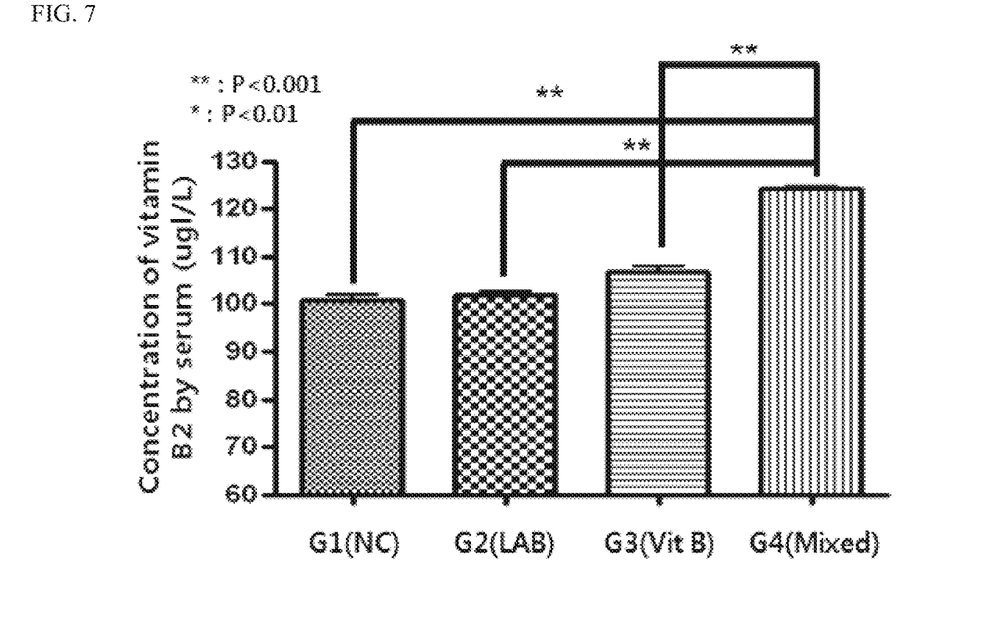
FIG. 7 graphically shows a change in the serum vitamin B2 level of each white rat administered with probiotics and a vitamin B complex in Test Example 2.
Figure 8:
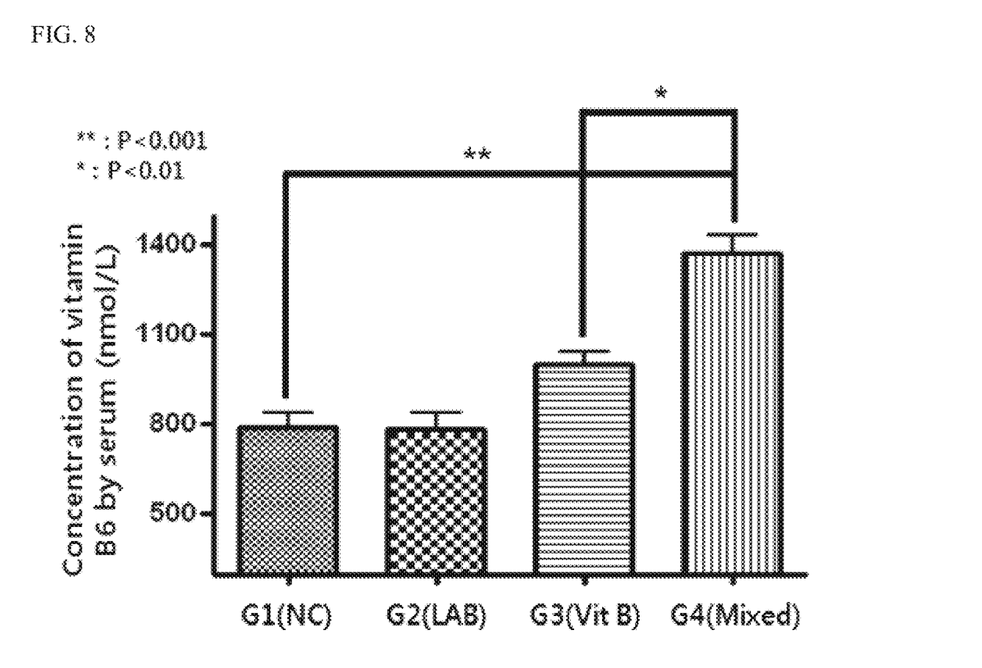
FIG. 8 graphically shows a change in the serum vitamin B6 level of each white rat administered with probiotics and a vitamin B complex in Test Example 2.

As shown in FIGS. 6 to 8 and Tables 7 to 9 above, the levels of vitamin B1, B2 and B6 in the serum of the group administered with the mixture of the probiotics and the vitamin B complex according to the present invention significantly increased compared to those in the groups administered with the probiotics and the vitamin B complex alone.

The above results indicate that the use of the mixture of the probiotics and the vitamin B complex according to the present invention promotes in vivo absorption of the vitamin B complex and promotes the conversion of metabolic energy to reduce blood cholesterol and triglyceride levels, thereby inhibiting arteriosclerosis, compared to when the probiotics and the vitamin B complex are used alone.

Test Example 3: Change in Intestinal Probiotics of White Rats

In order to examine the change in intestinal probiotics of white rats by administration of the probiotics and the vitamin B complex according to the present invention, gene expressions in the intestinal probiotics prepared in Example 1 were measured.

At 5 weeks after oral administration in Test Example 1, intestinal feces were isolated from G1 to G4, and DNA was extracted using an MP bio stool kit according to the manufacturer's protocol. Using the extracted DNA, real-time polymerase chain reaction (PCR) was performed using primers specific for *L. rhamnosus* and *E. faecium*. The results are shown in Tables 10 and 11 below and FIGS. 9 and 10.

TABLE 10

| | Mean ± SD | | | | |
|---|---|---|---|---|---|
| | G1 (NC) | G2 (LAB) | G3 (Vit B) | G4 (mixed) | P Value |
| *L. rhamnosus* (Nlog$_{10}$/1 g feces) | 6.856 ± 0.4687 | 9.686 ± 0.005477 | 7.412 ± 0.04817 | 9.450 ± 0.07280 | <0.0001 |

TABLE 11

| | Mean ± SD | | | | |
|---|---|---|---|---|---|
| | G1 (NC) | G2 (LAB) | G3 (Vit B) | G4 (mixed) | P Value |
| *E. faecium* (Nlog$_{10}$/1 g feces) | 3.944 ± 0.09607 | 8.866 ± 0.09290 | 5.582 ± 0.1366 | 8.376 ± 0.08050 | <0.0001 |

Figure 9:
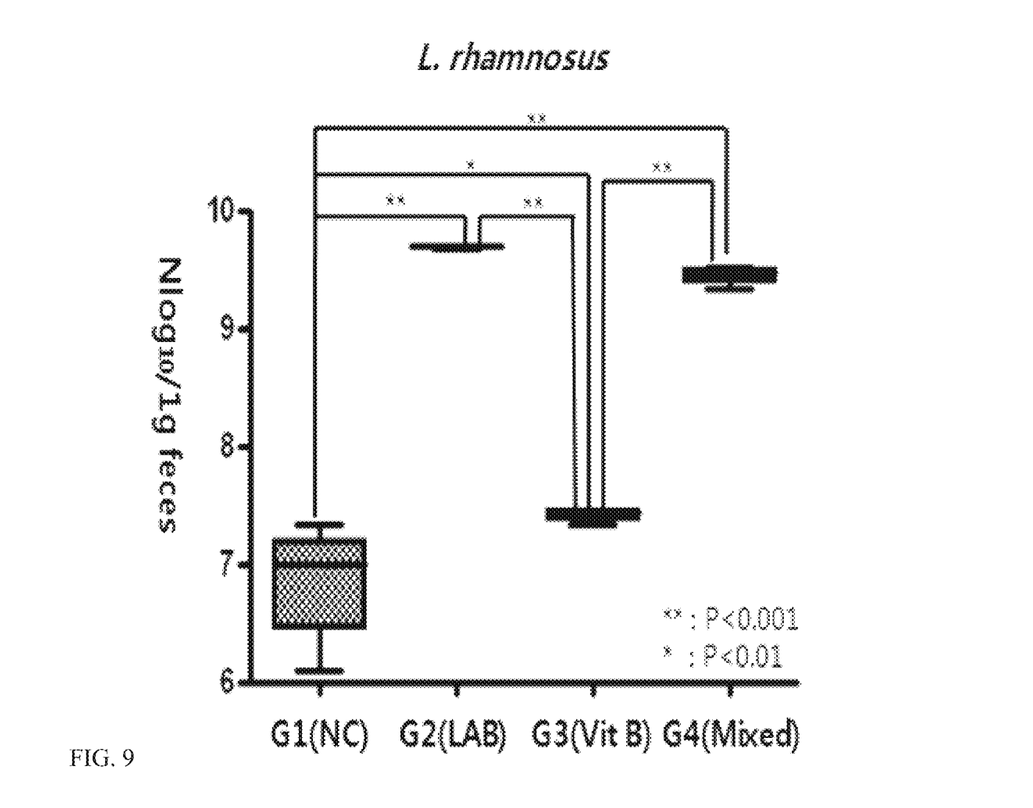
FIG. 9 graphically shows the distribution of *L. rhamnosus* in the feces of white rats as a result of each treatment of Example 1 in Test Example 3.
Figure 10:
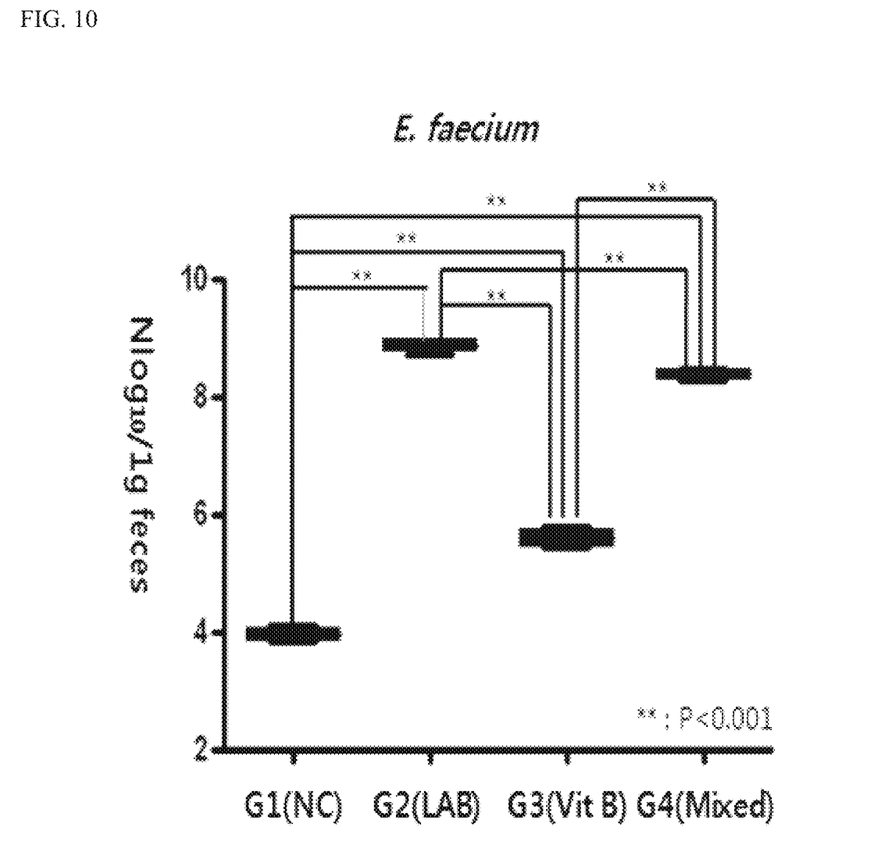
FIG. 10 graphically shows the distribution of *E. facecium* in the feces of white rats as a result of each treatment of Example 1 in Test Example 3.

As shown in FIGS. 9 and 10 and Tables 10 and 11 above, in the group (G4) administered with the mixture of the probiotics and the vitamin B complex according to the present invention, *L. rhamnosus* and *E. faecium* were detected in the intestines without being interfered by the vitamin B complex, similar to those in the group (G2) administered with the probiotics alone.

The above-described results indicate that when the mixture of the probiotics and the vitamin B complex according to the present invention is administered, it reduces cholesterol and triglyceride levels, thereby inducing a reduction in atherogenic index and promoting the absorption of the vitamin B complex.

Although the preferred embodiments of the present invention have been described in detail above, it will be obvious to those skilled in the art that the scope of the present invention is not limited to these embodiments and that various modifications and changes are possible without departing from the technical spirit of the present invention as defined in the appended claims.

What is claimed is:

1. A method for treating a lipid-related metabolic disease, the method comprising a step of administering to a subject in need of treatment a therapeutically effective amount of a composition containing probiotics and a vitamin B complex, wherein the lipid-related metabolic disease is selected from the group consisting of hyperlipidemia, arteriosclerosis, hypertension, and cardiovascular diseases;

wherein the probiotics comprise *Enterococcus faecium* and *Lactobacillus rhamnosus*;

wherein the vitamin B complex comprises vitamin B1, vitamin B2, vitamin B6 and vitamin B7; and wherein the probiotics promote the absorption of the vitamin B complex.

2. The method of claim 1, wherein the probiotics are contained in an amount of $3 \times 10^9$ to $6 \times 10^9$ CFU/g based on the total weight of the composition.

3. The method of claim 1, wherein the vitamin B complex further comprises two or more selected from the group consisting of vitamin B3, vitamin B12, salts thereof, and derivatives thereof.

* * * * *